United States Patent [19]

Evans et al.

[11] Patent Number: 5,032,383

[45] Date of Patent: Jul. 16, 1991

[54] ALUMINA HYDRATE-CONTAINING TOOTHPASTE

[75] Inventors: Kenneth A. Evans, Chalfont St. Peter; Kevin J. Wills, Stoke Poges; Anthony R. Emery, Chalfont St. Peter, all of United Kingdom

[73] Assignee: Alcan International Limited, Montreal, Canada

[21] Appl. No.: 309,368

[22] Filed: Feb. 13, 1989

[30] Foreign Application Priority Data

Feb. 12, 1988 [GB] United Kingdom ................. 8803329

[51] Int. Cl.$^5$ ............................................... A61K 7/16
[52] U.S. Cl. ....................................................... 424/49
[58] Field of Search ................................... 424/49, 52

[56] References Cited

U.S. PATENT DOCUMENTS

| | | | |
|---|---|---|---|
| 2,010,910 | 8/1935 | Atkins | 424/49 |
| 2,550,207 | 4/1951 | Tainter et al. | 424/49 |
| 3,003,919 | 10/1961 | Bruge | 424/49 |
| 3,662,060 | 5/1972 | Clippingdale et al. | 424/57 |
| 3,670,076 | 6/1972 | Muhler | 424/49 |
| 3,678,155 | 7/1972 | Clippingdale et al. | 424/52 |
| 3,822,345 | 7/1974 | Murray et al. | 424/52 |
| 3,957,968 | 5/1976 | Cordon . | |
| 4,034,076 | 7/1977 | Coulson et al. | 424/49 |
| 4,046,872 | 9/1977 | Mitchell et al. . | |
| 4,098,878 | 7/1978 | Baines et al. . | |
| 4,118,471 | 10/1978 | Pensak | 424/49 |
| 4,122,164 | 10/1978 | Mitchel et al. . | |
| 4,123,517 | 10/1978 | Baines et al. | 424/49 |
| 4,168,301 | 9/1979 | Pugh et al. | 424/49 |
| 4,212,856 | 7/1980 | Hoyles | 424/49 |
| 4,343,786 | 8/1982 | Baines et al. | 424/52 |
| 4,346,072 | 8/1982 | Baines et al. | 424/49 |
| 4,529,584 | 7/1985 | Mulvey et al. | 424/49 |
| 4,529,585 | 7/1985 | Hayes | 424/49 |
| 4,582,697 | 4/1986 | Cristol et al. | 423/629 |
| 4,781,982 | 11/1988 | Musselman et al. | 424/49 |

FOREIGN PATENT DOCUMENTS

| | | |
|---|---|---|
| 633845 | 12/1949 | United Kingdom . |
| 1277585 | 10/1969 | United Kingdom . |
| 1188353 | 4/1970 | United Kingdom . |
| 1310374 | 3/1973 | United Kingdom . |
| 1373001 | 11/1974 | United Kingdom . |
| 1442395 | 7/1976 | United Kingdom . |
| 1475252 | 6/1977 | United Kingdom . |
| 1491211 | 11/1977 | United Kingdom . |
| 1537823 | 1/1979 | United Kingdom . |
| 2009596 | 6/1979 | United Kingdom . |
| 1560913 | 2/1980 | United Kingdom . |
| 1587608 | 4/1981 | United Kingdom . |
| 2061727 | 5/1981 | United Kingdom . |

OTHER PUBLICATIONS

Kirk-Othmer Encyclopedia of Chemical Technology, 3rd Ed., vol. 2, (1978), pp. 218-244, Aluminum Oxide (Alumina).

Sumitomo Brochure (English Language Version), pp. 2, 8 and 9, Jun. 1985.

J. Scott, Effect of Seed and Temperature on the Particle Size of Bayer Hydrate, The British Aluminium Company, Ltd., New York, Feb. 1962.

Mordini and Cristol, "Production of Alumina Trihydrate for Non-Metallurgical Uses", Light Metals, pp. 325-336 (1983).

Mordini et al., C.A. 99:55753x (1983).

Evans, et al., C.A. 112:83887z (1990) of EP 328406, Aug. 16, 1989.

Evans et al., C.A. 112:83888A (1990) of EP 328407, Aug. 16, 1989.

*Primary Examiner*—Shep K. Rose
*Attorney, Agent, or Firm*—Browdy and Neimark

[57] ABSTRACT

This invention relates to toothpaste containing an alumina hydrate abrasive and flavoring.

According to the invention, there is provided a toothpaste containing flavoring and unmilled, precipitated alumina trihydrate as an abrasive, wherein the alumina trihydrate particles have a median particle size of at least 3 micrometers.

The median particle size of the alumina trihydrate is preferably below 30 micrometers, more preferably from 5 to 20 micrometers, and most preferably 8 to 12 micrometers.

It has been found that the use of an unmilled alumina trihydrate, obtained by precipitation, reduces the amount of flavoring material required to obtain a given flavor strength when compared with an equivalent content of milled alumina trihydrate of similar particle size.

15 Claims, No Drawings

ALUMINA HYDRATE-CONTAINING TOOTHPASTE

This invention relates to toothpaste containing an alumina hydrate abrasive and flavoring.

Toothpaste normally contains flavoring to improve consumer acceptability and a variety of flavoring additives are added to toothpaste for this purpose. Toothpaste also contains a particulate abrasive such as alumina trihydrate, calcium carbonate, silica or dicalcium phosphate. The median particle size of the abrasive is generally not more than about 30 micrometers because particles having a larger size, e.g. 50 micrometers, tend to be perceived as "gritty" in texture which is undesirable in a toothpaste. As the particle size is reduced a "smoother" texture is obtained but the cleaning power of such particles becomes less. A good abrasive effect is generally not achieved with particles below about 3 micrometers. When alumina trihydrate is used as the abrasive, particles in this desired size range are generally produced by attrition milling of coarser material before it is incorporated into the toothpaste. Examples of such known toothpastes are given in GB-A-1277585, GB-A-1491211, CB-A-1537823, GB-A-1475252, GB-A-1587608, US-A-4122164, GB-A-1188353, US-A-3957968, GB-B-2009596, CB-A-1310374, GB-A-1373001, GB-A-1442395, US-A-4046872, US-A-4098878, GB-A-1560913, GB-B-2061727, and GB-A-633845.

It has been found that many abrasives used in toothpaste tend to affect the flavoring materials added to the toothpaste particularly after storage of the toothpaste, so that the flavour characteristics of the toothpaste perceived by the user are changed. It is believed that this effect is caused by chemical and/or physical reaction of the flavoring constituents with the abrasive. In order to obtain a toothpaste having a given flavour intensity it is usual to compensate for this effect by increasing the amount of flavoring material added and, as the cost of the flavoring commonly accounts for 30–60% of the raw material costs, addition of further flavoring is expensive.

It has now been found that the use of an unmilled alumina trihydrate, obtained by precipitation, reduces the amount of flavoring material required to obtain a given flavour strength when compared with an equivalent content of milled alumina trihydrate of similar particle size. It is believed that fracture of the alumina trihydrate particles during milling produces an increased number of chemically and/or physically active sites on the particles' surfaces which appear to be responsible, at least in part, for the perceived loss of flavour in toothpaste, particularly after storage.

According to the present invention there is provided a toothpaste containing flavoring and unmilled, precipitated alumina trihydrate as an abrasive, wherein the alumina trihydrate particles have a median particle size of at least 3 micrometers.

The median particle size of the alumina trihydrate is preferably below 30 micrometers, more preferably from 5 to 20 micrometers, and most preferably 8 to 12 micrometers.

The content of alumina trihydrate particles may be within the range normally used for abrasives in toothpaste, that is generally from 20 to 60% by weight. When the abrasive particles have a relatively narrow particle size distribution a relatively low abrasive content, e.g. 20 to 50% by weight, can be used to achieve the desired toothpaste viscosity.

The flavoring constituents may be those conventionally used in toothpaste, for example peppermint, spearmint and oil of wintergreen. The content of flavoring constituents may be that normally used in toothpaste, for example from 0.8 to 1.0% by weight, or less.

The toothpaste may contain other constituents which are conventionally used. A typical formulation is about 50% by weight of alumina trihydrate as abrasive, about 27% by weight of 70% w/w sorbitol syrup, about 1% by weight of sodium carboxymethyl cellulose, about 1.5% by weight of a surfactant such as sodium lauryl sulphate, about 0.2% by weight of sodium saccharin, about 0.2% by weight of benzoic acid, about 0.8% of sodium monofluoro phosphate, about 1% by weight of flavoring and the balance water. Peridontal reagents such as Hibitane (supplied by ICI plc) may also be present. The toothpaste may be made by a conventional method in which the constituents other than the surfactant and flavoring are mixed in a high-speed disperser. The paste is then transferred to a slow speed mixer where the surfactant and flavour are added and the product is de-aerated. The product is then sealed in containers such as tubes.

It has been found that an alumina trihydrate having a narrow particle size distribution can be added at a lower addition level than normal milled products to achieve a paste of the correct viscosity. This gives benefits of lower paste density and improved cost effectiveness. It is also known that total and soluble soda contents of alumina trihydrate affect the retained available fluoride in toothpaste. In general the lower the total and soluble soda the higher the retained available fluoride. Thus a reduction in the amount of aluminium trihydrate content is beneficial.

Preferably the particle size distribution for the alumina trihydrate particles, as defined by the ratio $(d_{10}-d_{90})/d_{50}$, is less than 1.3, and desirably less than 1.0, wherein $d_{10}$, $d_{50}$ and $d_{90}$ are the sizes for which 10%, 50% and 90%, respectively, of the particles are larger than that size.

Toothpastes according to the invention will be described by way of illustration in the following Examples. In the Examples the toothpaste formulations are as set out in Table 1.

TABLE 1

| Toothpaste Formulations | | | |
|---|---|---|---|
| | Formulation (% by weight) | | |
| | 1 | 2 | 3 |
| Alumina Trihydrate | 52.00 | 45.00 | 50.00 |
| Sorbitol (70% w/w) | 27.00 | 27.00 | 27.00 |
| Sodium Carboxymethyl Cellulose | 1.10 | 1.10 | 1.10 |
| Sodium Saccharin | 0.20 | 0.20 | 0.20 |
| Sodium Monofluorophosphate | 0.80 | 0.80 | 0.80 |
| Benzoic Acid | 0.15 | 0.15 | 0.15 |
| Sodium Lauryl Sulphate | 1.50 | 1.50 | 1.50 |
| Sodium Benzoate | 0.20 | 0.20 | 0.20 |
| Water | 16.20 | 23.20 | 16.20 |
| Flavour | 0.85 | 0.85 | 0.85 |
| Titania | — | — | 2.00 |
| Total | 100.00 | 100.00 | 100.00 |

EXAMPLES 1

Two toothpastes were made by the following procedure: 472.5 g of 70% w/v sorbitol syrup were added to a 1 liter stainless steel vessel mounted on a high speed disperser (OBS Dispermix DL fitted with a 70 mm mixing head). With the disperser operating at 1700 r.p.m., 17.5 g of sodium carboxymethyl cellulose were slowly added. 220 g of water were then added gradually with increasing mixer speed, followed by 3.5 g of sodium saccharin. The mixer speed was again increased and 910 g of alumina trihydrate slowly added to produce a well-dispersed paste.

The mix was transferred to a vacuum vessel (a Lang Vacumix paste mixer) and a solution of 26.25 g of sodium lauryl sulphate in 72 ml of water was added. The mixture was stirred under vacuum for 5 minutes and the vacuum released; this operation was repeated 3 times to ensure de-aeration of the paste. 14 g of flavour (48450-type supplied by Zimmermann Hobbs Ltd) was added and the mixture stirred under vacuum for 20 minutes. The toothpaste obtained was then transferred to sealed containers and stored for 3 months at room temperature.

One of the toothpastes was made using milled alumina trihydrate having a median particle size of 8.5 micrometers (produced by BA Chemicals Ltd. under the trade mark "BACO AF 260") and the other was made using an unmilled, precipitated alumina trihydrate of median particle size 9.5 micrometres.

After storage the toothpastes were tested by a tasting panel of 7 persons. 5 of the panel reported that the toothpaste containing the unmilled alumina trihydrate had the stronger flavour.

EXAMPLE 2

Samples of toothpaste were prepared by a standard method from precipitated alumina trihydrates having the particle size distributions referred to in Table 2.

TABLE 2

| Trihydrate Sample | Formulation | Particle Size Distribution (Micrometers) | | | |
|---|---|---|---|---|---|
| | | $d_{10}$ | $d_{50}$ | $d_{90}$ | $\frac{d_{10}-d_{90}}{d_{50}}$ |
| A | 1 | 21.0 | 9.5 | 3.5 | 1.84 |
| B | 2 | 15.4 | 10.4 | 5.5 | 0.95 |

To achieve the same toothpaste viscosity, it was found that the loadings of alumina trihydrate were 52% for sample A and 45% for sample B. As can be seen from the results of Table 2 the alumina trihydrate having the narrower particle size distribution as defined by the ratio $(d_{10}-d_{90})/d_{50}$ gave the benefit of a lower alumina trihydrate loading and consequently a lower toothpaste density.

EXAMPLE 3

Two samples of toothpaste were prepared by the method described in Example 1 but using formulation No. 3 of Table 1, the first using a milled alumina trihydrate having a mean grain size of 10.4 micrometres and the second using a precipitated alumina trihydrate having a mean grain size of 9.5 micrometres. The flavour used was the same as used in Example 1. The toothpastes obtained were then transferred to sealed containers and stored at 49° C. for 9 weeks.

Flavour profiles of the two toothpastes were determined by a commercial research organization specializing in flavour evaluation. The sensory characteristics of the two pastes were determined by ten trained panelists on the basis of:
  (a) odour,
  (b) flavour,
  (c) mouthfeel during flavour tasting,
  (d) aftertaste, and
  (e) mouthfeel during aftertaste.

The results showed that the toothpaste containing the precipitated alumina trihydrate was adjudged to have:
  (i) a stronger menthol odour,
  (ii) a stronger peppermint odour,
  (iii) a less sweet flavour,
  (iv) a stronger cooling sensation, and
  (v) a slightly stronger peppermint aftertaste than that containing the milled alumina trihydrate.

The significantly greater sweetness sensation of the milled alumina trihydrate-containing toothpaste was attributed by the panelists to it having a lower flavour strength.

Milled alumina trihydrates of 5 to 30 micrometres are normally manufactured from coarse precipitated material of about 60 micrometres using a fluid energy mill, see British Patent 1,537,823.

Various methods can be used to prepare precipitated alumina trihydrates. For example, J. Scott ('Effect of Seed and Temperature on the Particle Size of Bayer Hydrate', paper presented at the International Symposium on the Extractive Metallurgy of Aluminium, New York, February 1962) reported that a 10.5 micrometres precipitated alumina trihydrate can be produced by the following method:
  a. alumina trihydrate seed (4.1 micrometres) is obtained by wet sieving and elutriation of coarse Bayer alumina trihydrate.
  b. The seed at a concentration of 40 g per litre is added to sodium aluminate liquor (130 g/l $Na_2O$, 130 g/l $Al_2O_3$).
  c. The solution is then decomposed at 50° C.

A precipitated alumina trihydrate having a median particle size of 9 micrometres is also available commercially from Nippon Light Metal Company of Japan.

The flavouring materials in the toothpaste may be those conventionally used for this purpose. One common flavouring material is a combination of peppermint and spearmint, to which may be added a small amount of eucalyptus, oil of wintergreen or aniseed. Toothpaste intended for use by children may contain other flavours, such as orange and strawberry. It is believed that the improvement observed using an unmilled alumina trihydrate abrasive, as described above, is obtained with substantially all the flavouring materials in current use in toothpastes. Generally not more than 2% of flavouring is used.

Although heretofore the disclosed precipitated alumina trihydrate has been described as the sole abrasive in the toothpaste composition, it can be supplemented by one or more other abrasives such as calcium carbonate.

Furthermore the disclosed precipitated alumina trihydrate can be blended with milled alumina trihydrate if desired. Because of the viscosity considerations referred to previously it is desirable that any other abrasive material which is used to supplement the precipitated alumina trihydrate has a particle size and a particle size distribution within the ranges preferred for the precipitated alumina trihydrate.

We claim:

1. In a toothpaste containing (i) a flavouring effective amount of a flavoring agent and (ii) an abrasion effective amount of alumina trihydrate as an abrasive having a particle size sufficiently great to have good abrasive effect but not so great as to provide a gritty texture, the improvement wherein
said alumina trihydrate consists essentially of unmilled, precipitated alumina trihydrate so as to provide said toothpaste with a stronger odor, a less sweet flavor and a slightly stronger aftertaste as compared to flavored toothpaste having milled alumina trihydrate particles of the same percentage by weight and of the same median particle size.

2. A toothpaste according to claim 1, in which the median particle size of the alumina trihydrate is below 30 micrometres.

3. A toothpaste according to claim 2, in which the median particle size of the alumina trihydrate is from 5 to 20 micrometres.

4. A toothpaste according to claim 3, in which the median particle size of the alumina trihydrate is from 8 to 12 micrometres.

5. A toothpaste according to claim 1 having a content of alumina trihydrate particles of from 20 to 60% by weight.

6. A toothpaste according to claim 5 having a content of alumina trihydrate particles of from 20 to 50% by weight and a particle size distribution for the alumina trihydrate particles as defined by the ratio $(d_{10}-d_{90})/d_{50}$ of less than 1.3.

7. A toothpaste according to claim 6 wherein the particle size distribution for the alumina trihydrate particles as defined by the ratio $(d_{10}-d_{90})/d_{50}$ is less than 1.0.

8. A toothpaste according to claim 1 in which the flavouring is present in an amount of up to 2% by weight.

9. A toothpaste according to claim 1 wherein the median particle size of the alumina trihydrate is below 30 micrometres, the abrasion-effective amount of alumina trihydrate is 20-60% by weight, and the flavoring-effective amount of flavoring agent is less than about 1.0%.

10. A toothpaste according to claim 9 wherein said flavoring agent is present in an amount of 0.8% to 1% by weight.

11. A toothpaste containing (i) flavoring-effective amount in the range of 0.8-1.0% by weight of a flavoring agent and (ii) an alumina trihydrate abrasive consisting essentially of an abrasion-effective amount in the range of 20-60% by weight of unmilled, precipitated alumina trihydrate, wherein the alumina trihydrate particles have a median particle size of 3—30 micrometers but not so great as to provide a gritty texture, said toothpaste being essentially free of milled alumina trihydrate and having less perceived loss of flavor after storage than toothpaste having milled alimina trihydrate particles of the same percentage by weight content and the same median particle size.

12. In a toothpaste containing (i) a flavoring agent and (ii) an abrasive including an abrasion effective amount of alumina trihydrate having a particle size sufficiently great to have good abrasive effect ut not so great as to provide a gritty texture, the improvement wherein
said abrasive consists of at least a first portion in an amount of at least 20% by weight based on the toothpaste of unmilled, precipitated alumina trihydrate so as to provide said toothpaste with less perceived loss of flavor after storage than toothpaste having milled alumina trihydrate particles of the same percentage by weight content and the same median particle size, said median particle size of said first portion being about 3-30 micrometers and having a particle size distribution as defined by the ratio $(d_{10}-d_{90})/d_{50}$ of less than 1.3, said toothpaste being generally free of milled alumina trihydrate.

13. In a toothpaste consisting essentially of (i) a flavoring agent and (ii) an abrasive including an abrasion effective amount of alumina trihydrate having a particle size sufficiently great to have good abrasive effective in the range of 20-60% by weight of said toothpaste consists of unmilled, precipitated alumina trihydrate so as to provide said toothpaste with less perceived loss of flavor after storage than toothpaste having milled alumina trihydrate particles of the same percentage by weight content and the same median particle size, said unmilled alumina trihydrate having a median particle size of about 3-30% micrometers and having a particle size distribution as defined by the ration $(d_{10}-d_{90})/d_{50}$ less than 1.3, said toothpaste being generally free of milled alumina trihydrate.

14. A toothpaste according to claim 6 wherein the particle size distribution for the alumna trihydrate particles as defined by the ratio $(d_{10}-d_{90})/d_{50}$ is less than 1.0.

15. A toothpaste according to claim 1 wherein the median particle size of the alumina trihydrate is about 3-30 micrometers, the content of alumina trihydrate particles is in the range of 20-50% by weight, and the particle size distribution for the alumina trihydrate particles as defined by the ratio $(d_{10}-d_{90})/d_{50}$ is less than 1.3.

* * * * *